United States Patent [19]

Klein

[11] Patent Number: 4,955,868

[45] Date of Patent: Sep. 11, 1990

[54] DISPOSABLE SAFETY MEDICAL SYRINGE

[76] Inventor: Edward Klein, 2 Professional Dr. Ste. 232, Gaithersburg, Md. 20879

[21] Appl. No.: 418,819

[22] Filed: Oct. 4, 1989

Related U.S. Application Data

[63] Continuation of Ser. No. 279,254, Nov. 28, 1988, abandoned, which is a continuation of Ser. No. 122,679, Nov. 19, 1987, abandoned.

[51] Int. Cl.$^5$ ............................................. A61M 5/32
[52] U.S. Cl. .................................. 604/198; 604/263
[58] Field of Search ............... 604/198, 195, 110, 192, 604/263, 187

[56] References Cited

U.S. PATENT DOCUMENTS

| | | | |
|---|---|---|---|
| 2,876,770 | 3/1959 | White | 604/198 |
| 3,995,629 | 12/1976 | Patel | 604/198 X |
| 4,639,249 | 1/1987 | Larson | 604/198 |
| 4,660,570 | 4/1987 | Dombrowski | 604/198 X |
| 4,664,654 | 5/1987 | Strauss | 604/198 |
| 4,767,413 | 8/1988 | Haber et al. | 604/232 X |
| 4,795,432 | 1/1989 | Karczmer | 604/110 |

FOREIGN PATENT DOCUMENTS 2079607 1/1982 United Kingdom ................. 604/198

*Primary Examiner*—John D. Yasko
*Attorney, Agent, or Firm*—James J. Brown

[57] ABSTRACT

A modification of a hypodermic syringe shielding the needle from user so that inadvertant puncture to the user of syringe will not occur before, during or after the injection of subject. This modification removes the necessity for capping or recapping the syringe. It is an improvement over prior devices in that the hypodermic needle is moved out of shield with out pressure of the syringe on subject being injected allowing for full view of needle during injection making venipuncture possible. The needle retracts automatically back in shield with release of pressure on shield handle (5) and syringe handle (7) by means of spring (2). Gasket (3) prevents movement of needle in shield by unintentional forces, and the plunger rod handle operates independently of retracting or protracting needle allowing for filling of syringe, aspiration of syringe and injecting with syringe. This device allows the safe use of a medical hypodermic syringe with out fear of contracting diseases the subject being injected may have by inadvertant puncture of user afer injecting subject. It also gives operator full visability of needle, control of needle and indendent action of exposing and needle and injecting with syringe or withdrawing blood of patient through springe.

1 Claim, 1 Drawing Sheet

DISPOSABLE SAFETY MEDICAL SYRINGE

This application is a continuation of Ser. No. 279,254 filed Nov. 28, 1988, now abandoned, which was a continuation of Ser. No. 122,679 filed Nov. 19, 1987 now abandoned.

An improved disposable medical syringe in which the user of the syringe is protected from inadvertant puncture to themselves befor, during, and after use of syringe until disposing of said syringe while still haveing full visabiliy of hypodermic needle through out the injection procedure making venipuncture and other delicate procedures possible with less risk of harming subject being injected.

The disadvantages of previous syringes of the disposable type is that the uncapped needle could easily puncture the operator of the syringe causing substances from the injection material or substances from the subject injected, to infiltrate user and cause serious illness or death. Recapping the needle in previous syringes is a stage of use which readily endangered the user of syringe to the possibility of being punctured.

In previous designs used to shield the needle from the user, the stated objecives of the devices were to either hide the needle from the subject being injected or sterilizing the needle for reuse. In those instances the needle is exposed by pushing the shield against the subject being injected, this pressure against the subject causes the shield to be retracted. The disadvantage to that procedure is that the user of the syringe has no visability as to where the needle is penetrating and could not properly manipulate the syringe as to locate and enter a blood vessel in subject for intravenous injections or for withdrawing blood from the subject. These previous designs do not allow the user of the syringe to use the syringe i the way he is trained to do so with a high degree of visibility of the needle. Another disadvantage of previous designs is that a constant pressure must be kept on the subject being injected by the shield while being used, leaving little ability of operator to easily change injection site.

DRAWING REFERECNCE NUMERALS

A. hypodermic syringe
B. hypodermic syringe shield
1. hypodermic needle
2. spring
3. gasket
4. wall of shield
5. shield handle
6. shield opening
7. syringe handle
8. plunger rod handle
9. syringe plunger
10. plunger rod
11. wall of syringe
12. syringe chamber The advantage of the pictured safty syringe is that the hypodermic needle is enclosed in a safty shield when unpacked from its sterile package. The user of said syringe must compress syringe handle(7) against shield handle(5) to cause needle(1) to fully extrude through shield opening(6). Releasing of the pressure between the syringe handle(7) and shield handle(5) will cause needle(1) to automacally go back into shield(B) due to spring(2) expanding back to normal unstressed length. The user of this safty syringe can extrude needle using one hand giving user full visability of needle and use of needle without first applying pressure on the subject being injected by needle; and allowing other hand free to guide needle into proper position or push plunger rod handle(8) to inject or retract plunger rod handle(8) to aspirate syringe before injecting; or to retract plunger rod handle(8) before drawing blood intravenously.

Upon release of syringe handle(7), needle(1) automatically goes back into shield protecting user from inadvertant puncturing of ones self. Due to gasket(3) the needle will remain unextruded and in its safty posistion even if dropped or shaken. Recapping of needle or necessity for immediate disposal of syringe is eliminated.

DR

FIG. 1. shows safty syringe with hypodermic needle(1) in retracted postion.

FIG. 2. shows safty syring with hypodermic needle (2) in extruded position.

FIG. 3. shows a more detailed close up of hypodermic syringe shield(B)

DESCRIPTION OF PREFERRED EMBODIMENTS

The disposable safty medical syringe consists of a hypodermic syringe(A) enclosed in a hypodermic syringe shield(b). The hypodermic syringe(A) is of normal varity used in medical procedures with hollow bore needle(1) tubular wall(11), plunger(9) attached to plunger rod(10), and is used in the way a hypodermic syringe is normally used; pushing of the plunger rod(10) in a direction which shortens the distance between plunger rod handle(8) and syringe handle(7) causing syringe plunger(9) to force liquid contents of syringe chamber(12) through hypodermic needle(1).

Figure 1:
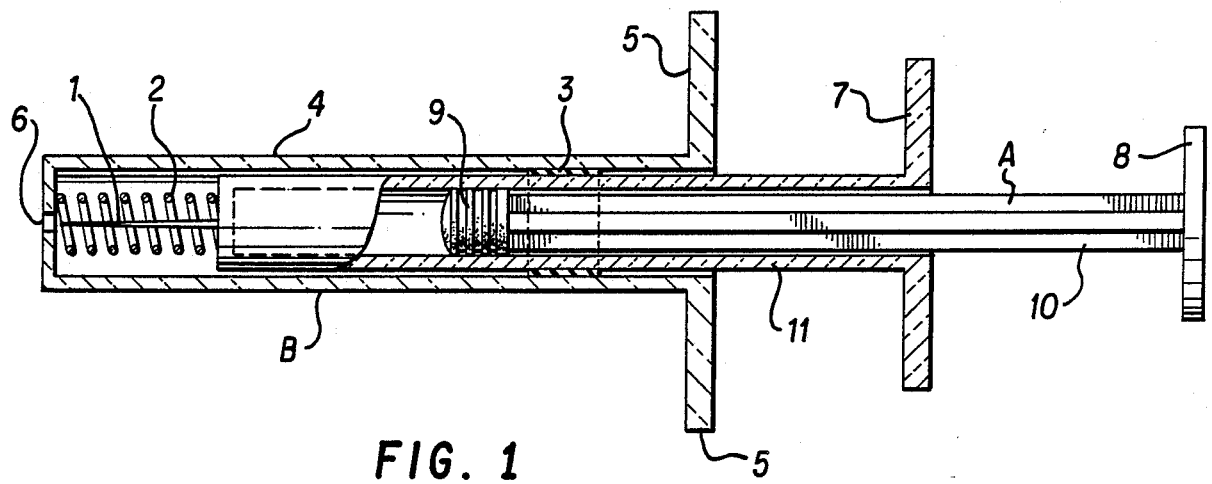
Figure 2:
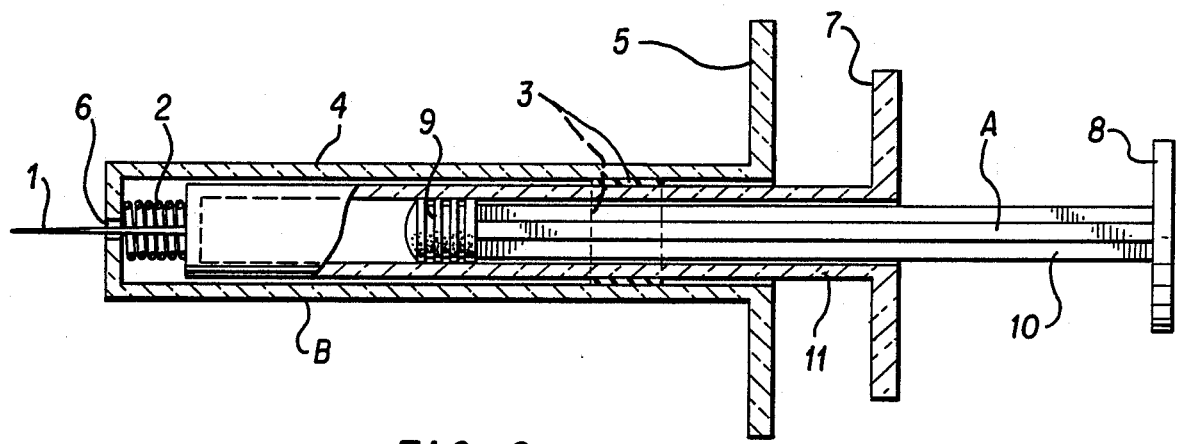
Figure 3:
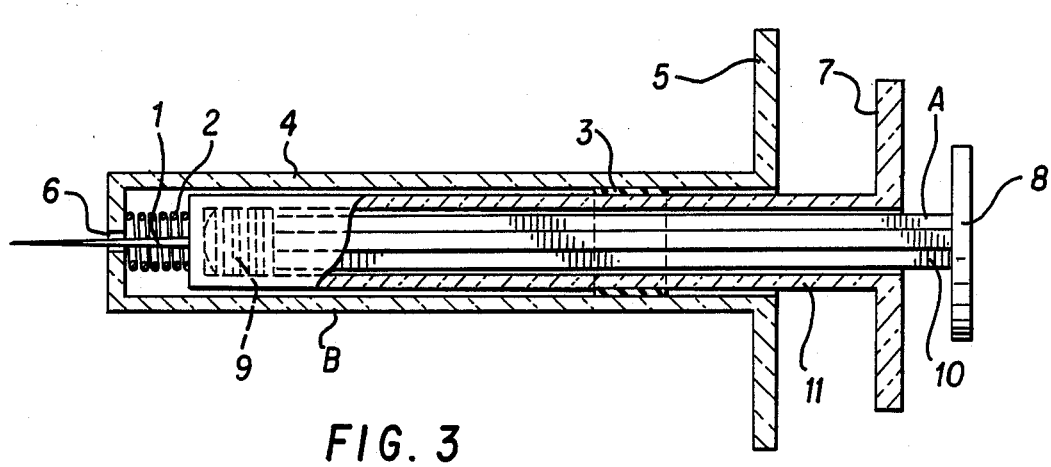

This hypodermic syringe(4) is placed into the hypodermic syringe shield(B) which is the embodiment of my improvement. The shield(B) consists of cylindrical tube which has a handle(5), shield opening(6), spring(2), syringe handle(7) and gasket(3). The syringe shield is slightly larger than the hypodermic syringe which will be inserted inside of it. The gasket(3) firmly surrounds the body of hypodermic syringe and fits with slight pressure on inner wall(4) of shield(B). This allows movement of hypodermic syringe(A) inside of shield(B) with slight pressure but not allow free movement of syringe(A) within syringe(B). When shield handle(5) is held in fixed posistion and syringe handle(7) is pushed towards it, the spring(2) is compressed by inner portion of hypodermic syring(A) and the needle(1) is extruded through opening(6). Upon release of syringe handle(7), spring(2) expands to original length pushing hypodermic syringe(A) back to original position causing needle(1) to automaticaly retract through shield opening(6). The movement of the hypodermic syringe(A) within hypodermic syringe shield(B) is independent of the plunger rod(10) or its handle(8), and therefore injection and expulsion of injectable substance is independent of protracting or retracting needle(1) from shield(B). In use, the disposable medical safty syringe would be removed from its sterile package and appear as it does in FIG. 1, with needle in retracted form. The user of device would then with index finger and thumb of same hand compress shield handle(5) and syring handle(7) together causing the needle to fully extrude through opening(6) in shield, with extended needle user would then puncture vial of substance to be injected with needle and draw back on plunger rod handle(8) with other hand. This would load syringe with injectable fluid. The user would then release pressure between handle(5) and handle(7) and needle would return into shield due to forces of spring(2). The user of syringe would then safely take syringe to area of use, and prepare subject for receiving injection. At that time, handle(7) and handle(5) would again be compressed causing needle(1) to fully extrude from shield(B) through opening(6) and puncture subject with needle in full view as would be done in unshielded syringe. After aspiration of syringe or venipuncture, rod(10) would be compressed downward towards handle(7) injecting fluid into subject. The needle is then with drawn from subject in usual manner still holding handle(5) and handle(7) together. After needle is removed from subject being injected pressure is released from handle(5) and handle(7) and needle automatically returns into shield due to spring (2). With the needle in its safty posiion, inadvertant puncture to the user of the syringe or other people in vicinity of syringe is advoided. The syringe would then be disposed of in a proper manner.

I claim:

1. A shield for use with a conventional unitary hypodermic syringe having a tubular body, piston and needle comprising a unitary cylindrical jacket of fixed length for enclosing and holding said hypodermic syringe partially within said jacket, said jacket having a constricted opening at one end for passage of the hypodermic needle of said syringe in response to displacement of the syringe within said jacket and being open at its other end to permit emplacement of said syringe so that the syringe piston and the portion of the syringe body proximate thereto extend beyond said jacekt and such that movement of said syringe piston in either direction within the tubular body of the syringe is independent of either said jacket or movement of the syringe body within said jacket, resilient spring means disposed within said jacket proximate to said constricted opening and around said syringe needle for maintaining said syringe in a retracted position within said jacket but permitting said unrestricted longitudinal displacement of the syringe in either direction within the jacket to cause passage of the needle through said constricted opening in the unitary jacket.

* * * * *